(12) United States Patent
MacDonald et al.

(10) Patent No.: US 7,705,078 B2
(45) Date of Patent: Apr. 27, 2010

(54) ANTIMICROBIAL POLYMERIC FILM

(75) Inventors: William Alasdair MacDonald, Guisborough (GB); Julia Elizabeth Friend Angold, Thatcham (GB); David Brown, Guisborough (GB)

(73) Assignee: DuPont Teijin Films U.S. Limited Partnership, Chester, VA (US)

( * ) Notice: Subject to any disclaimer, the term of this patent is extended or adjusted under 35 U.S.C. 154(b) by 0 days.

(21) Appl. No.: 11/630,366

(22) PCT Filed: Jun. 20, 2005

(86) PCT No.: PCT/GB2005/002424

§ 371 (c)(1), (2), (4) Date: Aug. 23, 2007

(87) PCT Pub. No.: WO2006/000755

PCT Pub. Date: Jan. 5, 2006

(65) Prior Publication Data

US 2008/0044458 A1 Feb. 21, 2008

(30) Foreign Application Priority Data

Jun. 25, 2004 (GB) ................................. 0414333.5

(51) Int. Cl.
*C08K 3/10* (2006.01)
(52) U.S. Cl. ...................... 524/403; 523/122
(58) Field of Classification Search ................. 524/403; 523/122
See application file for complete search history.

(56) References Cited

U.S. PATENT DOCUMENTS

| | | | |
|---|---|---|---|
| 3,959,526 A | 5/1976 | Swerlick | |
| 4,375,494 A | 3/1983 | Stokes | |
| 5,151,331 A | 9/1992 | Beeson et al. | |
| 5,296,238 A | 3/1994 | Sugiura et al. | |
| 5,328,724 A | 7/1994 | Deak | |
| 5,441,717 A | 8/1995 | Ohsumi et al. | |
| 5,556,699 A | 9/1996 | Niira et al. | |
| 5,639,466 A | 6/1997 | Ford et al. | |
| 5,728,467 A | 3/1998 | Watanabe et al. | |
| 6,004,660 A | 12/1999 | Topolski et al. | |
| 6,641,842 B2 | 11/2003 | Laridon et al. | |
| 2002/0192259 A1 | 12/2002 | Voris et al. | |
| 2003/0091767 A1 | 5/2003 | Podhajny | |
| 2003/0108608 A1 | 6/2003 | Laridon et al. | |
| 2003/0215521 A1 | 11/2003 | Laridon et al. | |
| 2004/0017021 A1 | 1/2004 | Laridon et al. | |
| 2008/0107880 A1 | 5/2008 | Kliesch et al. | |

FOREIGN PATENT DOCUMENTS

| | | |
|---|---|---|
| DE | 4106165 | 9/1992 |
| DE | 19506395 | 8/1995 |
| DE | 20313065 | 3/2004 |
| EP | 0582823 | 2/1994 |
| EP | 0846418 A | 6/1998 |
| EP | 1097805 | 5/2001 |
| EP | 1314550 | 5/2003 |
| GB | 0838708 | 6/1960 |
| JP | 3083905 | 4/1991 |
| JP | 6010126 | 2/1994 |
| JP | 06287324 | 10/1994 |
| JP | 07053770 | 2/1995 |
| JP | 08001079 | 1/1996 |
| JP | 09048094 | 2/1997 |
| JP | 09183707 | 7/1997 |
| JP | 09248883 | 9/1997 |
| JP | 10016158 | 1/1998 |
| JP | 10114602 | 5/1998 |
| JP | 10245495 | 9/1998 |
| JP | 11048431 | 2/1999 |
| JP | 2001064162 | 3/2001 |
| JP | 2002103527 | 4/2002 |
| JP | 2006199852 | 8/2006 |
| TW | 200418718 | 10/2004 |
| WO | WO 00/53413 | 9/2000 |
| WO | WO 02/55301 | 7/2002 |
| WO | WO 02/62577 | 8/2002 |
| WO | WO 02/089766 | 11/2002 |

(Continued)

OTHER PUBLICATIONS

National Industrial Chemicals Notification and Assessment Scheme; "Silver Sodium Hydrogen Zirconium Phosphate"; Full Public Report; Mar. 11, 2004; File No. STD/1081; 40 pp; NICNAS, Sydney, AU.

(Continued)

*Primary Examiner*—Kriellion A Sanders
(74) *Attorney, Agent, or Firm*—RatnerPrestia

(57) ABSTRACT

An anti-microbial polymeric film comprising a polymeric substrate layer and an inorganic anti-microbial compound of formula (I): $Ag_aH_bA_cM_2(PO_4)_3 \cdot nH_2O$ wherein: A is at least one ion selected from an alkali or alkaline earth metal ion; M is a tetravalent metal ion; a is in the range 0.4 to 0.5; b and c are positive numbers such that (a+b+mc)=1; m is the valence of metal A; and $0 \leq n \leq 6$, wherein the anti-microbial compound is present in the substrate layer in an amount of from about 0.05 to about 0.7% of by weight of the polymeric material of the substrate layer; and the use of said inorganic anti-microbial compound for providing an antimicrobial polymeric film having reduced haze.

11 Claims, No Drawings

FOREIGN PATENT DOCUMENTS

| | | |
|---|---|---|
| WO | WO 02/089766 A1 | 11/2002 |
| WO | WO03049914 | 6/2003 |
| WO | WO2004063254 | 7/2004 |
| WO | WO2004064523 | 8/2004 |
| WO | WO 2006073853 | 7/2006 |

OTHER PUBLICATIONS

Attalla, Giancarlo; International Search Report; Aug. 24, 2009; European Patent Office, The Netherlands.

ANTIMICROBIAL POLYMERIC FILM

This application is the national phase filing of PCT Application No. GB/2005/002424, filed Jun. 20, 2005, which claims priority of GB of Application No. 0414333.5, filed Jun. 25, 2004.

The present application is concerned with anti-microbial polymeric film, particularly polyester film.

The preparation of polymeric films having anti-microbial properties is well-known. Such films are of use in the provision of anti-microbial surfaces, for example in medical and catering environments. The anti-microbial properties are imparted using an anti-microbial agent. The preparation of such films typically involves disposing the anti-microbial agent into the polymer matrix or on one or more surface(s) as a coating. Desirably, the anti-microbial agent should have a broad spectrum of activity over different microbes, and a low toxicity profile for higher organisms. Metal ions, particularly silver ions, have long been known to exhibit anti-fungal, anti-bacterial and anti-algal activity (hereinafter referred to as anti-microbial activity). Recently, it has been proposed to use an anti-microbial metal ion supported on zirconium phosphate, as disclosed in, for instance, U.S. Pat. No. 5,441,717, JP-A-3/83905 and U.S. Pat. No. 5,296,238. U.S. Pat. No. 5,556,699 discloses use of a zeolite antibacterial agent in a coextruded or laminated film comprising inter alia PVC, polyolefin, polyester and/or polyvinyl alcohol layers, which is useful for packaging foods and medical equipment. U.S. Pat. No. 5,639,466 discloses a packaging film comprising an anti-bacterial composition of (a) 5-40% lactide or lactic acid oligomer; (b) 0-20% organic plasticiser; and (c) 60-95% lactic acid polymer or copolymer, which is coated as a layer of at least 5 μm in thickness on a polymeric substrate. EP-A-0846418 discloses antibacterial films comprising an inorganic and/or organic antibacterial agent and a hydrophilic substance, which is suitable for use in food packaging. Anti-microbial agents are relatively expensive and the consumer must generally balance anti-microbial efficacy against cost. It would be desirable to provide more economical anti-microbial films for a given anti-microbial efficacy, or films having greater anti-microbial efficacy for a given cost.

Since the anti-microbial agent is typically added during the polymerisation stage of film manufacture, it must be thermally stable at the processing temperatures experienced during polymer and film preparation. Any decomposition of the anti-microbial agent reduces the anti-microbial activity of the film, may cause discolouration in the film, and increases the cost of a film which is required to produce a defined level of anti-microbial activity. It would be desirable to provide anti-microbial films in which the anti-microbial agent exhibits less decomposition, particularly during film manufacture.

A further problem with existing anti-microbial films is that the presence of the anti-microbial agent can cause undesirable haze and reduction in gloss, relative to a film without the anti-microbial agent.

It is an object of this invention to address one or more of the afore-mentioned problems, and particularly to provide an anti-microbial film which exhibits good optical properties, including low haze and high gloss.

DETAILED DESCRIPTION OF THE INVENTION

As used herein, the term "anti-microbial" means microbicidal activity or microbe growth inhibition in a microbe population. In one embodiment, the microbe(s) is/are selected from the group consisting of *Aspergillus niger*, *Staphylococcus aureus* and *Escherichia coli*. In one embodiment, the term "anti-microbial" means a greater than 1 log reduction, preferably a greater than 2 log reduction, preferably a greater than 3 log reduction, and more preferably a greater than 4 log reduction in the growth of a population of microbes relative to a control.

According to the present invention, there is provided an anti-microbial polymeric film comprising a polymeric substrate layer and an inorganic anti-microbial compound of formula (I):

$$Ag_a H_b A_c M_2(PO_4)_3 \cdot nH_2O \quad \text{(I)}$$

wherein:

A is at least one ion selected from an alkali or alkaline earth metal ion;

M is a tetravalent metal ion;

a is in the range 0.4 to 0.5;

b and c are positive numbers such that (a+b+mc)=1;

m is the valence of metal A; and $0 \leq n \leq 6$, wherein the anti-microbial compound is present in the substrate layer in an amount of from about 0.05 to about 0.7% of by weight of the polymeric material of the substrate layer.

The inventors have unexpectedly found that, for a given final silver content in the polymeric substrate layer of an anti-microbial film, a relatively low concentration of an anti-microbial agent which has a relatively high fraction of silver ions improves the film's optical properties relative to a relatively high concentration of an anti-microbial agent which has a relatively low fraction of silver ions.

Preferably the anti-microbial compound is present in an amount of from about 0.1 to about 0.7%, preferably from about 0.2 to about 0.6, and more preferably from about 0.3 to about 0.5% by weight of the polymeric material of the substrate layer. Preferably, the silver is present in an amount of from about 5 to about 15%, preferably from about 7 to about 13%, preferably from about 8 to about 12%, and preferably from about 9 to 11% by weight of the anti-microbial compound.

The anti-microbial compounds of formula (I) may be prepared according to the methods described in U.S. Pat. No. 5,441,717 or U.S. Pat. No. 5,296,238. The anti-microbial silver ion is supported on the zirconium phosphate. The metal A is preferably selected from lithium, sodium, potassium, magnesium and calcium, and is preferably sodium. The metal M is preferably selected from zirconium, titanium and tin, preferably from zirconium and titanium, and is preferably zirconium. The value of the parameter "b" is preferably at least 0.2, more preferably in the range of 0.2 to 0.5. In one embodiment, the value of the parameter "b" is on the range 0.2 to 0.3. In one embodiment, the antimicrobial compound is selected from $Ag_{0.46}Na_{0.29}H_{0.25}Zr_2(PO_4)_3$.

In a preferred embodiment, the particle size of the anti-microbial compound is such that the volume distributed mean particle diameter is in the range of 0.4 to 10 μm, preferably 1.0 to 6.0 μm, and more preferably 1.0 to 3.0 μm.

The anti-microbial compound is incorporated within the polymeric matrix of the substrate layer. The anti-microbial compound may be added prior to, during or after the polymerisation reaction to synthesise the substrate polymer, but is preferably added after polymerisation and prior to film formation.

In a further aspect of the invention, there is provided the use of an anti-microbial compound of formula (I) in the manufacture of an anti-microbial polymeric film comprising a polymeric substrate layer, for the purpose of improving the haze of said film, wherein said anti-microbial compound is present in the substrate layer in an amount of from about 0.05 to about 0.7% by weight of the polymeric material of the substrate layer.

In a further aspect of the invention, there is provided a method of improving the haze of an anti-microbial polymeric film comprising a polymeric substrate layer by incorporating therein an anti-microbial compound of formula (I) in an amount of from about 0.05 to about 0.7% by weight of the polymeric material of the substrate layer.

The polymeric substrate layer is a self-supporting film or sheet by which is meant a film or sheet capable of independent existence in the absence of a supporting base. The substrate may be formed from any suitable film-forming polymer, including polyolefin (such as polyethylene and polypropylene), polyamide (including nylon), PVC and polyester. The polymeric substrate may be oriented, such as oriented polypropylene or polyethylene terephthalate (PET), or amorphous, as discussed in more detail below. In a preferred embodiment, the substrate is polyester, and particularly a synthetic linear polyester.

The preferred synthetic linear polyesters of the substrate may be obtained by condensing one or more dicarboxylic acids or their lower alkyl (up to 6 carbon atoms) diesters, eg terephthalic acid, isophthalic acid, phthalic acid, 2,5-, 2,6- or 2,7-naphthalenedicarboxylic acid, succinic acid, sebacic acid, adipic acid, azelaic acid, 4,4'-diphenyldicarboxylic acid, hexahydro-terephthalic acid or 1,2-bis-p-carboxyphenoxyethane (optionally with a monocarboxylic acid, such as pivalic acid) with one or more glycols, particularly an aliphatic or cycloaliphatic glycol, e.g. ethylene glycol, 1,3-propanediol, 1,4-butanediol, neopentyl glycol and 1,4-cyclohexanedimethanol. An aromatic dicarboxylic acid is preferred. An aliphatic glycol is preferred. Polyesters or copolyesters containing units derived from hydroxycarboxylic acid monomers, such as $\omega$-hydroxyalkanoic acids (typically $C_3$-$C_{12}$) such as hydroxypropionic acid, hydroxybutyric acid, p-hydroxybenzoic acid, m-hydroxybenzoic acid, or 2-hydroxynaphthalene-6-carboxylic acid, may also be used.

In a preferred embodiment, the polyester is selected from polyethylene terephthalate and polyethylene naphthalate. Polyethylene terephthalate (PET) is particularly preferred.

The substrate may comprise one or more discrete layers of the above film-forming materials. The polymeric materials of the respective layers may be the same or different. For instance, the substrate may comprise one, two, three, four or five or more layers and typical multi-layer structures may be of the AB, ABA, ABC, ABAB, ABABA or ABCBA type.

In one embodiment, the substrate is a bilayer substrate wherein one layer is a heat-sealable layer. Heat-sealable layers are well-known in the art and include polymeric materials such as polyester, EVA or modified polyethylene. In one embodiment, the heat-sealable layer comprises a linear polyester resin, particularly a copolyester resin derived from one or more of the dicarboxylic acid(s) with one or more of the glycol(s) noted above. In such a multilayer substrate, the antimicrobial agent may be present in each layer. Alternatively, the antimicrobial agent is present in the layer open to the atmosphere, i.e. the layer which is not laminated or heat-sealed to a surface.

Formation of the substrate may be effected by conventional techniques well-known in the art. Conveniently, formation of the substrate is effected by extrusion, in accordance with the procedure described below. In general terms the process comprises the steps of extruding a layer of molten polymer, quenching the extrudate and orienting the quenched extrudate in at least one direction.

The substrate may be uniaxially-oriented, but is preferably biaxially-oriented, as noted above. Orientation may be effected by any process known in the art for producing an oriented film, for example a tubular or flat film process. Biaxial orientation is effected by drawing in two mutually perpendicular directions in the plane of the film to achieve a satisfactory combination of mechanical and physical properties.

In a tubular process, simultaneous biaxial orientation may be effected by extruding a thermoplastics polymer tube which is subsequently quenched, reheated and then expanded by internal gas pressure to induce transverse orientation, and withdrawn at a rate which will induce longitudinal orientation.

In the preferred flat film process, the substrate-forming polymer is extruded through a slot die and rapidly quenched upon a chilled casting drum to ensure that the polymer is quenched to the amorphous state. Orientation is then effected by stretching the quenched extrudate in at least one direction at a temperature above the glass transition temperature of the polyester. Sequential orientation may be effected by stretching a flat, quenched extrudate firstly in one direction, usually the longitudinal direction, i.e. the forward direction through the film stretching machine, and then in the transverse direction. Forward stretching of the extrudate is conveniently effected over a set of rotating rolls or between two pairs of nip rolls, transverse stretching then being effected in a stenter apparatus. Alternatively, the cast film may be stretched simultaneously in both the forward and transverse directions in a biaxial stenter. Stretching is effected to an extent determined by the nature of the polymer, for example polyethylene terephthalate is usually stretched so that the dimension of the oriented film is from 2 to 5, more preferably 2.5 to 4.5 times its original dimension in the or each direction of stretching. Typically, stretching is effected at temperatures in the range of 70 to 125° C. Greater draw ratios (for example, up to about 8 times) may be used if orientation in only one direction is required. It is not necessary to stretch equally in the machine and transverse directions although this is preferred if balanced properties are desired.

A stretched film may be, and preferably is, dimensionally stabilised by heat-setting under dimensional restraint at a temperature above the glass transition temperature of the polyester but below the melting temperature thereof, to induce crystallisation of the polyester. The actual heat-set temperature and time will vary depending on the composition of the film but should not be selected so as to substantially degrade the mechanical properties of the film. Within these constraints, a heat-set temperature of about 135° to 250° C. is generally desirable, as described in GB-A-838708.

Where the substrate comprises more than one layer, preparation of the substrate is conveniently effected by coextrusion, either by simultaneous coextrusion of the respective film-forming layers through independent orifices of a multi-orifice die, and thereafter uniting the still molten layers, or, preferably, by single-channel coextrusion in which molten streams of the respective polymers are first united within a channel leading to a die manifold, and thereafter extruded together from the die orifice under conditions of streamline flow without intermixing thereby to produce a multi-layer polymeric film, which may be oriented and heat-set as hereinbefore described. Formation of a multi-layer substrate may also be effected by conventional lamination techniques, for example by laminating together a preformed first layer and a preformed second layer, or by casting, for example, the first layer onto a preformed second layer. Where the substrate comprises a heat-sealable layer, the heat-sealable layer may also be applied by conventional coating techniques.

In one embodiment, the substrate is heat-shrinkable. The shrinkage characteristics of a film are determined by the stretch ratios and heat-setting conditions employed during its manufacture, as is well-known to the skilled person. In general, the shrinkage behaviour of a film which has not been heat-set corresponds to the degree to which the film has been stretched during its manufacture. In the absence of heat-setting, a film which has been stretched to a high degree will exhibit a high degree of shrinkage when subsequently exposed to heat; a film which has only been stretched by a small amount will only exhibit a small amount of shrinkage. Heat-setting has the effect of providing dimensional stability to a stretched film, and "locking" the film in its stretched state. Thus, the shrinkage behaviour of a film under the action of heat depends on whether, and to what extent, the film was heat-set after the stretching operation(s) effected during its manufacture. In general, a film which has experienced a temperature $T_1$ during the heat-setting operation will exhibit substantially no shrinkage below temperature $T_1$ when subsequently exposed to heat after manufacture. Accordingly, in order to impart shrinkage characteristics, the substrate is not heat-set or partially heat-set at a relatively low temperature and/or using a relatively short duration after stretching has been effected. A shrinkable substrate may exhibit shrinkage in one or both directions of the film. The degree of shrinkage in one dimension may be the same as, or different to, the degree of shrinkage in the orthogonal direction. Preferably, the shrinkage is in the range of from about 0 to about 80% when placed in a water bath at 100° C. for 30 seconds, preferably from about 5 to about 80%, preferably from about 10 to bout 80%, more preferably from about 10 to 60%.

The polymeric substrate may conveniently contain any of the additives conventionally employed in the manufacture of polymeric films. Thus, agents such as dyes, pigments, voiding agents, lubricants, anti-oxidants, radical scavengers, UV absorbers, fire retardants, thermal stabilisers, anti-blocking agents, surface active agents, slip aids, optical brighteners, gloss improvers, prodegradents, viscosity modifiers and dispersion stabilisers may be incorporated in the substrate as appropriate. In particular the substrate may comprise a particulate filler. The filler may, for example, be a particulate inorganic filler or an incompatible resin filler or a mixture of two or more such fillers. Particulate inorganic fillers include metal or metalloid oxides, such as alumina, silica (especially precipitated or diatomaceous silica and silica gels) and titania, calcined china clay and alkaline metal salts, such as the carbonates and sulphates of calcium and barium. Suitably, the substrate layer is unfilled or filler is typically present in only small amounts, generally not exceeding 0.5% and preferably less than 0.2% by weight of the substrate polymer.

The components of the composition of a layer may be mixed together in a conventional manner. For example, by mixing with the monomeric reactants from which the layer polymer is derived, or the components may be mixed with the polymer by tumble or dry blending or by compounding in an extruder, followed by cooling and, usually, commination into granules or chips. Masterbatching technology may also be employed.

The substrate layer is suitably of a thickness between about 5 and 350 μm, preferably from 12 to about 250 μm and particularly from about 20 to about 75 μm.

In one embodiment, anti-microbial film is coated with a coating layer which is sufficient to provide a barrier to water vapour and/or oxygen. In one embodiment, the coating is sufficient to provide a water vapour transmission rate in the range of 0.01 to 10 g/100 inches$^2$/day, preferably 0.01 to 0.1 g/100 inches$^2$/day, and in one embodiment 0.1 to 1.0 g/100 inches$^2$/day, and/or an oxygen transmission rate in the range of 0.01 to 10 cm$^3$/100 inches$^2$/day/atm, preferably 0.01 to 1 cm$^3$/100 inches$^2$/day/atm, and in one embodiment 0.1 to 1 cm$^3$/100 inches$^2$/day/atm. Suitable coat weights are in the range of 0.01 to 14 g/m$^2$, preferably 0.02 to 1.5 g/m$^2$. Conventional barrier coatings include PVDC, PCTFE, PE, PP, EVOH and PVOH. PVDC layers are particularly suitable for providing a barrier to both gas and water vapour; EVOH and PVOH layers are particularly suitable for providing a barrier to gas; while PCTFE, PE and PP layers are particularly suitable for providing a barrier to water vapour. Suitable layers are known in the art and are disclosed, for instance, in U.S. Pat. No. 5,328,724 (EVOH), U.S. Pat. No. 5,151,331 (PVDC), U.S. Pat. No. 3,959,526 (PVDC), U.S. Pat. No. 6,004,660 (PVDC and PVOH). Suitable PVDC polymeric layers are copolymers of 65 to 96% by weight of vinylidene chloride and 4 to 35% of one or more comonomers such as vinyl chloride, acrylonitrile, methacrylonitrile, methyl methacrylate, or methyl acrylate, and are generally referred to as saran. A suitable grade contains about 7 weight percent methacrylonitrile, 3 weight percent methyl methacrylate, and 0.3 weight percent itaconic acid comonomers.

In a further embodiment, the anti-microbial film may be coated with a sealant coating sufficient to provide a heat-seal strength of from 100 g/in to 2500 g/in when heat-sealed to itself according to the test method described herein. Preferably the, heat-seal strength is at least about 300 g/in, preferably at least 500 g/in, preferably at least 750 g/in. Suitable coat weights are in the range of 0.5 to 14 g/m$^2$, preferably 1.0 to 10 g/m$^2$. Suitable heat-sealable or sealant coatings include ethylene vinyl acetate (EVA), amorphous polyesters (APET), olefinic polymers such as polyethylene (PE), caprolactone, acid copolymers such as ethylene methacrylic acid (EMAA), ionomers such as Surlyn, and styrenic copolymers such as styrene isoprene styrene (SIS). Suitable layers are well-known in the art. U.S. Pat. No. 4,375,494 and U.S. Pat. No. 6,004,660 describe amorphous copolyester sealant layers. Suitable copolyesters may comprise an aromatic dicarboxylic acid and an aliphatic dicarboxylic acid. Suitable aromatic dicarboxylic acids include terephthalic acid, isophthalic acid, phthalic acid, or 2,5-, 2,6- or 2,7-naphthalenedicarboxylic acid, and suitable aliphatic dicarboxylic acids include succinic acid, sebacic acid, adipic acid, azelaic acid, suberic acid or pimelic acid. A preferred aromatic dicarboxylic acid is terephthalic acid. Preferred aliphatic dicarboxylic acids are selected from sebacic acid, adipic acid and azelaic acid. A particularly preferred aliphatic diacid is sebacic acid. The concentration of the aromatic dicarboxylic acid present in the copolyester is preferably in the range from 40 to 80, more preferably 45 to 65, and particularly 50 to 60 mole % based on the dicarboxylic acid components of the copolyester. The glycol component of the copolyester of the coating layer preferably contains from 2 to 8, more preferably 2 to 4 carbon atoms. Suitable glycols include ethylene glycol, 1,3-propanediol, 1,3-butane diol, 1,4-butanediol, 1,5-pentane diol, neopentyl glycol, 2,2-dimethyl-1,3-propanediol, diethylene glycol, triethylene glycol and 1,4-cyclohexanedimethanol. An aliphatic glycol, particularly ethylene glycol or 1,4-butanediol, is preferred. In a particularly preferred embodiment, the aliphatic glycol is 1,4-butanediol. Such copolyesters preferably have a glass transition point of less than 10° C., more preferably less than 0° C., particularly in the range from −50° C. to 0° C., and especially −50° C. to −10° C., and a melting point in the range from 90° C. to 250° C., more preferably 110° C. to 175° C., and particularly 110° C. to 155° C. Particularly preferred examples of such copolyesters are (i) copolyesters of azeleic acid and terephthalic acid with an aliphatic glycol, preferably ethylene glycol; (ii) copolyesters of adipic acid and terephthalic acid with an aliphatic glycol, preferably ethylene glycol; and (iii) copolyesters of sebacic acid and terephthalic acid with an aliphatic glycol, preferably butylene glycol. Preferred polymers include a copolyester of sebacic acid/terephthalic acid/butylene glycol (preferably having the components in the relative molar ratios of 45-55/55-45/100, more preferably 50/50/100) having a glass transition point ($T_g$) of −40° C. and a melting point ($T_m$) of 117° C.), and a copolyester of azeleic acid/terephthalic acid/ethylene glycol (preferably having the components in the relative molar ratios of 40-50/60-50/100, more preferably 45/55/100) having a $T_g$ of −15° C. and a $T_m$ of 150° C. Suitable EVA polymers may be obtained from DuPont as Elvax™ resins. Typically, these resins have a vinyl acetate content in the range of 9% to 40%, and typically 15% to 30%.

In a further embodiment, a coating layer provides both barrier and heat-seal properties, and PVDC coatings are suitable in this regard. In an alternative embodiment, a heat-sealable coating may be applied to one surface of the substrate, and a barrier layer on the other surface of the substrate. In one embodiment, said coating layer(s) providing barrier and/or heat seal properties do not contain an antimicrobial agent.

A coating layer may be applied to the substrate either in-line or off-line. The coating may be applied to an already-oriented substrate. However, application of a coating composition is preferably effected before or during the stretching operation(s). For instance, the coating may be applied to the film substrate between the two stages (longitudinal and transverse) of a biaxial stretching operation. Thus, the film substrate may be stretched firstly in the longitudinal direction over a series of rotating rollers, coated with the coating composition, and then stretched transversely in a stenter oven, and preferably then heat-set. The coating composition may be applied to the polymer film substrate in aqueous or organic solution, in a dispersion or in an emulsion, suitably in neat form, by any suitable conventional coating technique such a gravure roll coating, reverse roll coating, dip coating, bead coating, slot coating, electrostatic spray coating, extrusion coating or melt coating. Prior to deposition of a coating composition onto the substrate, the exposed surface thereof may, if desired, be subjected to a chemical or physical surface-modifying treatment, as are well-known in the art, in order to improve the bond between that surface and the subsequently applied coating. Physical surface-modifying treatments include flame treatment, ion bombardment, electron beam treatment, ultra-violet light treatment and corona discharge.

A coating layer typically has a thickness in the range of about 0.01 to 14.0 μm. In one embodiment, the coating thickness is no more than about 5 μm, preferably no more than about 4 μm, preferably no more than about 2 μm, and preferably no more than about 1 μm. Preferably, the coating layer is in the range of about 0.02 to about 1.5 μm, preferably 0.02 to about 1.0 μm. In one embodiment, the coating layer thickness is 0.5 microns or greater.

The film preferably has a % of scattered visible light (haze) of <15%, preferably <12%, preferably <9%, preferably <6%, more preferably <3.5% and particularly <2%, measured according to the standard ASTM D 1003.

The 60° gloss value of the film (measured as described herein) is preferably at least 70, more preferably at least 80, and more preferably at least 85.

The films obtainable using the invention may be used to provide an anti-microbial surface in a variety of applications, such as in medical and catering environments and equipment, and in food packaging. Other applications include restrooms, garbage disposals, animal feed troughs, schools, swimming pool areas, automobile fixtures, public access fixtures, public seating, public transportation fixtures, toys, and other industrial, agricultural, commercial or consumer products.

The following test methods may be used to determine certain properties of the polymeric film:

(i) Haze (% of scattered transmitted visible light) is measured using a Gardner Hazegard System XL-211, according to ASTM D 1003.

(ii) 60° gloss value of the film surface is measured using a Dr Lange Reflectometer REFO 3 (obtained from Dr Bruno Lange, GmbH, Dusseldorf, Germany) according to DIN 67530. Reflection was measured at three angles (20°, 60° and 85°) and measurements were carried out in both the machine and transverse directions of the film.

(iii) Water vapour transmission rate is measured according to ASTM D3985.

(iv) Oxygen transmission rate is measured according to ASTM F1249.

(v) Anti-microbial efficacy against bacteria was assessed using the "plate contact method" against 0.4 ml of $10^5$ cells/ml in Na/K phosphate buffer with 22 hours exposure. Film samples were tested against *Klebsiella pneumoniae* ATCC #4352 and *Staphylococcus aureus* ATCC #6538 in duplicate in two separate experiments (vi) Anti-microbial efficacy against fingi was assessed using a method based on ISO-846 using *Aspergillus niger* ATTC 6275. Each sample was inoculated with 0.1 ml of a solution of $10^5$ fungal spores per ml, and incubated at 29° C. for up to 35 days. The fungal growth was assess by visual observation of the samples for samples where fungal growth that has localised to droplets. Efficacy is then rated in three categories:

| Observed growth in droplets | Category |
| --- | --- |
| Droplets have dark growth; many spores | A |
| Droplets have light growth; few/no spores | B |
| Droplets have no or scarce growth | C |

The rating of a given sample is then the number of droplets in each category.

(vii) Heat-seal strength is measured by heat-sealing a film sample to itself (coating layer contacted with coating layer) at 250° F. under 30 psi with 0.35 seconds dwell time in a Sentinel® apparatus.

(viii) Shrinkage is measured by placing a film sample (a strip of approximately 1 inch) in a water bath at 100° C. for 30 seconds and the difference in length before and after heat treatment used to calculate the shrinkage.

The invention is further illustrated by the following examples. It will be appreciated that the examples are for illustrative purposes only and are not intended to limit the invention as described above. Modification of detail may be made without departing from the scope of the invention.

EXAMPLES

Example 1

Comparative

An anti-microbial polyethylene terephthalate (PET) polymer was prepared by addition of an anti-microbial agent (ALPHASAN® RC5000 antimicrobial additive; $Ag_{0.18}Na_{0.57}H_{0.25}Zr_2(PO_4)_3$, available from Milliken) to the polyester polymerisation process. A conventional direct esterification reaction on a 2600 kg scale reactor was used. After water distillation, pressure let-down and stabiliser addition, the monomer was transferred to the polycondensation vessel. At this point, with the monomer at 265° C., the anti-microbial agent was added as a 30% slurry in glycol, which equates to a level of 1% anti-microbial agent by weight in the final polymer. The polycondensation reaction was carried out after the addition of 300 ppm $Sb_2O_3$ catalyst to provide a PET having an in-line IV of 0.636.

A molten web of the anti-microbial PET was co-extruded at a temperature of 275° C. with a copolyester of ethylene terephthalate and ethylene isophthalate (82%:18%) in a conventional manner from a slot die onto the polished surface of a cooled rotating drum. The cooled film was first stretched under a draw ratio of 3.33 in the direction of extrusion at a temperature of 76-79° C. The film was then heated to a temperature of 85° C. and then stretched in the sideways direction under a draw ratio of 3.5 at a temperature of 110° C. The biaxially stretched film was heat-set in a three-stage oven at temperatures of 220, 210 and 200° C. by conventional means. The final film thickness was 20 microns, the anti-microbial layer being 16 microns and the heat-seal layer being 4 microns.

Example 2

An anti-microbial agent (ALPHASAN® RC2000 antimicrobial additive; $Ag_{0.46}Na_{0.29}H_{0.25}Zr_2(PO_4)_3$ available from Milliken) was mixed with PET polymer to give a composition containing 0.40% by weight of anti-microbial agent. The composition was coextruded using the procedure described above. The cooled film was first stretched under a draw ratio of 3.2 in the direction of extrusion at a temperature of 72-75° C. The film was then heated to a temperature of 85° C. and then stretched in the sideways direction under a draw ratio of 3.4 at a temperature of 110° C. The biaxially stretched film was heat-set in a three-stage oven at temperatures of 220, 210 and 200° C. by conventional means. The final film thickness was 20 microns, the anti-microbial layer being 16 microns and the heat-seal layer being 4 microns.

The films of the above Examples were analysed using the tests described herein and the results are given in Table 1. The Control film corresponds to the film of Example 1 without the anti-microbial agent.

TABLE 1

| Sample | Gloss at 60° | Haze |
|---|---|---|
| Control | 143 | 2.2 |
| Example 1 (Comparative) | 34 | 26.5 |
| Example 2 | 156 | 5.7 |

It can be seen from Table 1 that the gloss and haze of film of Example 2 compares well with the control film, and is superior to the film of (comparative) Example 1 in terms of gloss and haze.

Anti-microbial efficacy was assessed as described hereinabove. Table 2 below shows the correlation between the number and percentage reduction of live bacteria with the log reduction thereof. Thus, a log reduction of 2 equates to 99% of the bacteria being killed.

TABLE 2

| Percent Reduction | Log Reduction | Number of Live Bacteria* (CFU/ml) |
|---|---|---|
| 0 | 0.0 | 1,000,000 (1 × 10⁶) |
| 50 | 0.3 | 500,000 (5 × 10⁵) |
| 90 | 1.0 | 100,000 (1 × 10⁵) |
| 99 | 2.0 | 10,000 (1 × 10⁴) |
| 99.9 | 3.0 | 1,000 (1 × 10³) |
| 99.99 | 4.0 | 100 (1 × 10²) |

Both Example 1 (comparative) and Example 2 were found to be effective in providing a significant anti-bacterial effect against both bacteria in the test method used.

The invention claimed is:

1. An anti-microbial polyester film comprising a polyester substrate layer and an inorganic anti-microbial compound of formula (I):

$$Ag_aH_bA_cM_2(PO_4)_3 \cdot nH_2O \qquad (I)$$

wherein:
A is at least one metal selected from alkali and alkaline earth metals;
M is a tetravalent metal;
a is in the range 0.4 to 0.5;
b and c are positive numbers such that (a+b+mc)=1;
m is the valence of metal ion A; and
$0 \leq n \leq 6$;
wherein the anti-microbial compound is present in the substrate layer in an amount of from about 0.05 to about 0.7% by weight of the polyester material of the substrate layer and wherein the film is self-supporting.

2. The film according to claim 1, wherein said polyester substrate comprises polyethylene terephthalate.

3. The film according to claim 1, wherein the haze is less than 15%.

4. The film according to claim 1, wherein the gloss is at least 70.

5. The film according to claim 1, wherein the anti-microbial compound is present in an amount of from about 0.2 to about 0.6% by weight of the polyester material of the substrate layer.

6. The film according to claim 1, wherein the metal A is selected from the group consisting of lithium, sodium, potassium, magnesium and calcium.

7. The film according to claim 1, wherein the metal A is sodium.

8. The film according to claim 1, wherein the metal M is selected from the group consisting of zirconium, titanium and tin.

9. The film according to claim 1, wherein the parameter "b" is at least 0.2.

10. A method of manufacturing an antimicrobial polyester film comprising a polyester substrate layer, the method comprising incorporating in the polyester substrate layer an anti-microbial compound of formula (I):

$$Ag_aH_bA_cM_2(PO_4)_3 \cdot nH_2O \qquad (I)$$

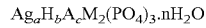

wherein:
A is at least one metal selected from alkali and alkaline earth metals;
M is a tetravalent metal;
a is in the range 0.4 to 0.5;
b and c are positive numbers such that (a+b+mc)=1;
m is the valence of metal A; and
$0 \leq n \leq 6$;
wherein said anti-microbial compound is present in the substrate layer in an amount of from about 0.05 to about 0.7% by weight of the polyester material of the substrate layer, and wherein the anti-microbial film is self-supporting and has a haze of less than 15%.

11. A method of making an anti-microbial film comprising a polyester substrate layer, said method comprising incorporating in the polyester substrate layer an anti-microbial compound of formula (I):

$$Ag_aH_bA_cM_2(PO_4)_3 \cdot nH_2O \quad (I)$$

wherein:
A is at least one metal selected from alkali and alkaline earth metals;
M is a tetravalent metal;
a is in the range 0.4 to 0.5;
b and c are positive numbers such that (a+b+mc)=1;
m is the valence of metal A; and
$0 \leq n \leq 6$;
wherein the anti-microbial compound is present in an amount of from about 0.05 to about 0.7% by weight of the polyester material of the substrate layer and wherein the film is self-supporting and has a haze of less than 15%.

* * * * *